United States Patent [19]
Poetsch et al.

[11] Patent Number: 5,800,735
[45] Date of Patent: Sep. 1, 1998

[54] 1,3-DIOXANES, AND LIQUID-CRYSTALLINE MEDIUM

[75] Inventors: Eike Poetsch, Mühltal; Harald Lannert, Crumbach; Joachim Krause, Dieburg; Kazuaki Tarumi, Seeheim, all of Germany

[73] Assignee: Merck Patent Gesellschaft mit Beschrankter Haftung, Germany

[21] Appl. No.: 774,692

[22] Filed: Dec. 26, 1996

[30] Foreign Application Priority Data

Dec. 29, 1995 [DE] Germany .................. 195 49 123.8

[51] Int. Cl.$^6$ .................. C09K 19/34; C09K 19/20
[52] U.S. Cl. .................. 252/299.61; 252/299.61; 428/1
[58] Field of Search .................. 252/299.61, 299.63, 252/299.67; 428/1

[56] References Cited

U.S. PATENT DOCUMENTS 4,877,547 10/1989 Weber et al. .................. 252/299.61
5,030,383 7/1991 Scheuble et al. .................. 252/299.61

Primary Examiner—Shean C. Wu
Attorney, Agent, or Firm—Millen, White, Zelano & Branigan, P.C.

[57] ABSTRACT 1,3-Dioxanes of the formula I

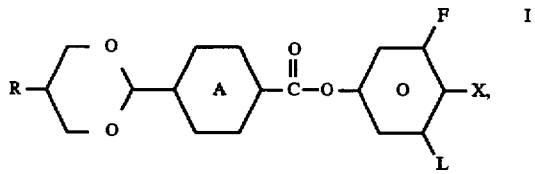

in which R, X, L and

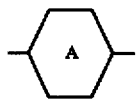

are as defined below, are suitable as components of liquid-crystalline media.

11 Claims, No Drawings

1,3-DIOXANES, AND LIQUID-CRYSTALLINE MEDIUM

The invention relates to 1,3-dioxanes of the general formula I

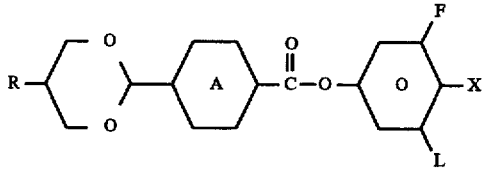

in which

R is H, an alkyl or alkenyl radical having 1 to 15 carbon atoms which is unsubstituted, monosubstituted by CN or $CF_3$, or at least monosubstituted by halogen, where, in addition, one or more $CH_2$ groups in these radicals can be replaced, in each case independently of one another, by —O—, —S—,

—CO—, —CO—O—, —O—CO— or —O—CO—O— in such a way that O atoms are not linked directly to one another,

is (a) trans-1,4-cyclohexylene,
(b) 1,4-phenylene, in which one or two CH groups can also be replaced by N,
(c) 1,4-cyclohexenylene, where the radicals (b) and (c) can be monosubstituted or polysubstituted by fluorine, X is F, Cl, halogenated alkyl, alkoxy or alkenyl having 1-5 carbon atoms, and L is H or F.

The invention furthermore relates to the use of these compounds as components of liquid-crystalline media, and to liquid-crystal and electro-optical display elements containing the novel liquid-crystalline media.

The compounds of the formula I can be used as components of liquid-crystalline media, in particular for displays based on the principle of the twisted cell, the guest-host effect, the effect of deformation of aligned phases or the effect of dynamic scattering.

The invention had the object of finding novel, stable, liquid-crystalline or mesogenic compounds which are suitable as components of liquid-crystalline media and in particular simultaneously have relatively low viscosity and relatively high dielectric anisotropy.

It has now been found that compounds of the formula I are eminently suitable as components of liquid-crystalline media. In particular, they have relatively. low viscosities. They can be used to obtain stable liquid-crystalline media having a broad mesgphase range and advantageous optical and dielectric anisotropy values. Furthermore, these media have very good low-temperature behavior.

BACKGROUND OF THE INVENTION 1,3-Dioxanes of the formula I in which X=L=F are covered by the general formula in EP 0 387 032, but are not named.

EP 0 447 565 discloses 1,3-dioxanes of the formula

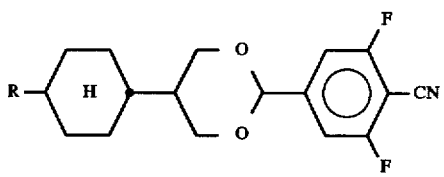

and their use in STN mixtures.

U.S. Pat. No. 5,322,638 claims 1,3-dioxanes of the formula

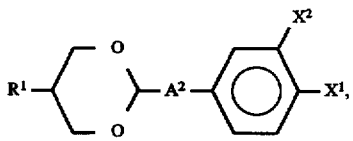

in which $R^1$ is an alkenyl radical, $A^2$ is a 1,4-phenyl ring or trans-1,4-cyclohexylene ring, $X^1$ is F or Cl, and $X^2$ is fluorine.

EP 0 400 861 discloses phenyldioxanes of the formula

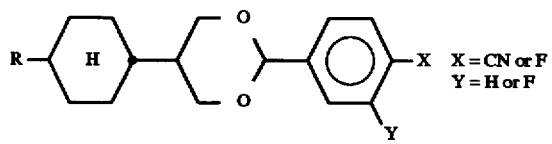

X = CN or F
Y = H or F

In view of the very wide variety of applications of 1,3-dioxanes having a high Δε, however, it was desirable to have available further compounds of high nematogeneity which have properties precisely customized to the particular applications.

SUMMARY OF THE INVENTION

In addition, the provision of compounds of the formula I very generally considerably broadens the range of liquid-crystalline substances which are suitable, from various applicational points of view, for the preparation of liquid-crystalline mixtures.

The compounds of the formula I have a broad range of applications. Depending on the choice of substituents, these compounds can be used as base materials from which liquid-crystalline media are predominantly composed; however, it is also possible to add compounds of the formula I to liquid-crystalline base materials from other classes of compound in order, for example, to modify the dielectric and/or optical anisotropy of a dielectric of this type and/or to optimize its threshold voltage and/or its viscosity. The novel compounds are distinguished, in particular, by their broad mesophase range while having good viscosity properties and Δε values.

In the pure state, the compounds of the formula I are colorless and form liquid-crystalline mesophases in a temperature range which is favorably located for electro-optical use. They are stable chemically, thermally and to light.

The invention thus relates to the compounds of the formula I and to the use of these compounds as components of liquid-crystalline media. The invention furthermore relates to liquid-crystalline media comprising at least one compound of the formula I and to liquid-crystal display elements, in particular electro-optical display elements, containing such media.

Preferred compounds of the formula I are those of the sub-formulae I1 to I5:

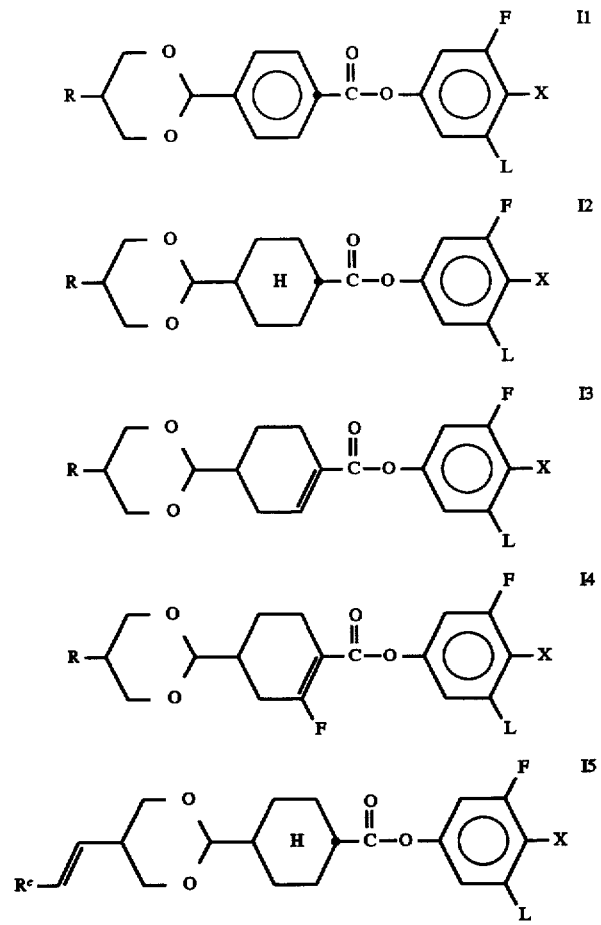

In the compounds of the formula I, R is preferably straight-chain alkyl or alkenyl having 1–5 carbon atoms. The alkenyl radical is preferably 1E-alkenyl, 3E-alkenyl or 4-alkenyl.

L is preferably F.

X is preferably F, Cl, $OCF_3$, $OCHF_2$, $CF_3$, $CHF_2$, $OCHFCF_3$, $OCHFCHF_2$, $OCH_2CF_3$, $OC_2F_5$, $OC_3F_7$, $OCH=CHF$, $OCF=CHF$, $OCH=CF_2$, $OCF=CF_2$, $OCF_2CHFCF_3$, in particular F, $OCF_3$, $OCHF_2$, $OCHFCF_3$, $OCHFCHF_2$ and $OCH=CF_2$.

Particular preference is given to compounds of the formula I in which X=L=F.

If R in the compounds of the formula I is an alkyl radical and/or an alkoxy radical, this can be straight-chain or branched. It is preferably straight-chain, has 2, 3, 4, 5, 6 or 7 carbon atoms and accordingly is preferably ethyl, propyl, butyl, pentyl, hexyl, heptyl, ethoxy, propoxy, butoxy, pentoxy, hexoxy or heptoxy, furthermore methyl, octyl, nonyl, decyl, undecyl, dodecyl, tridecyl, tetradecyl, pentadecyl, methoxy, octoxy, nonoxy, decoxy, undecoxy, dodecoxy, tridecoxy or tetradecoxy.

Oxaalkyl is preferably straight-chain 2-oxapropyl (=methoxymethyl), 2- (=ethoxymethyl) or 3-oxabutyl (=2-methoxyethyl), 2-, 3- or 4-oxapentyl, 2-, 3-, 4- or 5-oxahexyl, 2-, 3-, 4-, 5- or 6-oxaheptyl, 2-, 3-, 4-, 5-, 6- or 7-oxaoctyl, 2-, 3-, 4-, 5-, 6-, 7- or 8-oxa-nonyl, or 2-, 3-, 4-, 5-, 6-, 7-, 8- or 9-oxadecyl.

If R is an alkyl radical in which one $CH_2$ group has been replaced by —CH=CH—, this can be straight-chain or branched. It is preferably straight-chain and has 2 to 10 carbon atoms. Accordingly, it is in particular vinyl, prop-1- or -2-enyl, but-1-, -2- or -3-enyl, pent-1-, -2-, -3- or -4-enyl, hex-1-, -2-, -3-, -4- or -5-enyl, hept-1-, -2-, -3-, -4-, -5- or -6-enyl, oct-1-, -2-, -3-, -4-, -5-, -6- or -7-enyl, non-1-, -2-, -3-, -4-, -5-, -6-, -7- or -8-enyl, or dec-1-, -2-, -3-, -4-, -5-, -6-, -7-, -8- or -9-enyl.

If R is an alkyl radical in which one $CH_2$ group has been replaced by —O— and one has been replaced by —CO—, these are preferably adjacent. These thus contain one acyloxy group —CO—O— or one oxycarbonyl group —O—CO—.

These are preferably straight-chain and have 2 to 6 carbon atoms.

Accordingly, they are in particular acetoxy, propionyloxy, butyryloxy, pentanoyloxy, hexanoyloxy, acetoxymethyl, propionyloxymethyl, butyryloxymethyl, pentanoyloxymethyl, 2-acetoxyethyl, 2-propionyloxyethyl, 2-butyryloxyethyl, 3-acetoxypropyl, 3-propionyloxypropyl, 4-acetoxybutyl, methoxycarbonyl, ethoxycarbonyl, propoxycarbonyl, butoxycarbonyl, pentoxycarbonyl, methoxycarbonylmethyl, ethoxycarbonylmethyl, propoxycarbonylmethyl, butoxycarbonylmethyl, 2-(methoxycarbonyl)ethyl, 2-(ethoxycarbonyl)ethyl, 2-(propoxycarbonyl)ethyl, 3-(methoxycarbonyl)propyl, 3-(ethoxycarbonyl)propyl or. 4-(methoxycarbonyl)butyl.

If R is an alkyl radical in which one $CH_2$ group has been replaced by unsubstituted or substituted —CH=CH— and an adjacent $CH_2$ group has been replaced by CO or CO—O or O—CO—, this can be straight-chain or branched. It is preferably straight-chain and has 4 to 13 carbon atoms. Accordingly, it is in particular acryloyloxymethyl, 2-acryloyloxyethyl, 3-acryloyloxypropyl, 4-acryloyloxybutyl, 5-acryloyloxypentyl, 6-acryloyloxyhexyl, 7-acryloyloxyheptyl, 8-acryloyloxyoctyl, 9-acryloyloxynonyl, 10-acryloyloxydecyl, methacryloyloxymethyl, 2-methacryloyloxyethyl, 3-methacryloyloxypropyl, 4-methacryloyloxy-butyl, 5-methacryloyloxypentyl, 6-methacryloyloxyhexyl, 7-methacryloyloxyheptyl, 8-methacryloyloxyoctyl 9-methacryloyloxynonyl.

If R is an alkyl or alkenyl radical which is monosubstituted by CN or $CF_3$, this radical is preferably straight-chain and substitution by CN or $CF_3$ is in the ω-position.

If R is an alkyl or alkenyl radical which is at least monosubstituted by halogen, this radical is preferably straight-chain and halogen is preferably F or Cl. In the case of multiple substitution, halogen is preferably F. The resultant radicals also include perfluorinated radicals. In the case of monosubstitution, the fluorine or chlorine substituent can be in any desired position, but preferably in the ω-position.

Compounds of the formula I which contain wing groups R which are suitable for addition polymerization reactions are suitable for the preparation of liquid-crystalline polymers.

Compounds of the formula I containing branched wing groups R may occasionally be of importance due to better solubility in the customary liquid-crystalline base materials, but in particular as chiral dopes if they are optically active. Smectic compounds of this type are suitable as components for ferroelectric materials.

Compounds of the formula I having $S_A$ phases are suitable, for example, for thermally addressed displays.

Branched groups of this type generally contain not more than one chain branch. Preferred branched radicals R are isopropyl, 2-butyl (=1-methylpropyl), isobutyl (=2- methylpropyl), 2-methylbutyl, isopentyl (=3-methylbutyl), 2-methylpentyl, 3-methylpentyl, 2-ethylhexyl, 2-propylpentyl, isopropoxy, 2-methylpropoxy, 2-methylbutoxy, 3-methylbutoxy, 2-methylpentoxy, 3-methylpentoxy, 2-ethylhexoxy, 1-methylhexoxy- and 1-methylheptoxy.

If R is an alkyl radical in which two or more CH$_2$ groups have been replaced by —O— and/or -CO—O—, this may be straight-chain or branched. It is preferably branched and has 3 to 12 carbon atoms. Accordingly, it is in particular biscarboxymethyl, 2,2-biscarboxyethyl, 3,3-biscarboxypropyl, 4,4-biscarboxybutyl, 5,5-biscarboxypentyl, 6,6-biscarboxyhexyl, 7,7-biscarboxyheptyl, 8,8-biscarboxyoctyl, 9,9-biscarboxynonyl, 10,10-biscarboxydecyl, bis (methoxycarbonyl)methyl, 2,2-bis(methoxycarbonyl)ethyl, 3,3-bis(methoxycarbonyl)propyl, 4,4-bis(methoxycarbonyl) butyl, 5,5-bis(methoxycarbonyl)pentyl, 6,6-bis (methoxycarbonyl)hexyl, 7,7-bis(methoxycarbonyl)-heptyl, 8,8-bis(methoxycarbonyl)octyl, bis (ethoxycarbonyl) methyl, 2,2-bis(ethoxycarbonyl)ethyl, 3,3-bis-(ethoxycarbonyl)propyl, 4,4-bis(ethoxycarbonyl)butyl or 5,5-bis(ethoxycarbonyl)hexyl.

Compounds of the formula I which contain wing groups R which are suitable for polycondensation reactions are suitable for the preparation of liquid-crystalline polycondensates.

The formula I covers the racemates of these compounds and the optical antipodes, and mixtures thereof.

Of these compounds of the formula I and the subformulae, preference is given to those in which at least one of the radicals present therein has one of the preferred meanings indicated.

The compounds of the formula I are prepared by methods known per se, as described in the literature (for example in the standard works, such as Houben-Weyl, Methoden der Organischen Chemie, Georg-Thieme-Verlag, Stuttgart), to be precise under reaction conditions which are known and suitable for the said reactions.

Use can also be made here of variants which are known per se, but which are not mentioned here in greater detail.

The compounds are accessible in a simple manner by forming the 1,3-dioxane ring by elimination of water in the reaction of the corresponding diol with the aldehyde, or by forming the substituent X directly via the corresponding hydrogen, OH, tosylate, triflate, bromine, iodine, metal or aldehyde derivative by processes known from the literature.

The novel compounds can be prepared, for example, as follows:

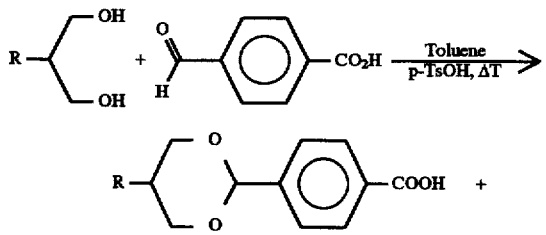

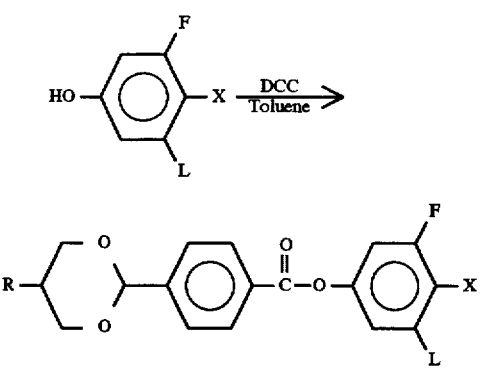

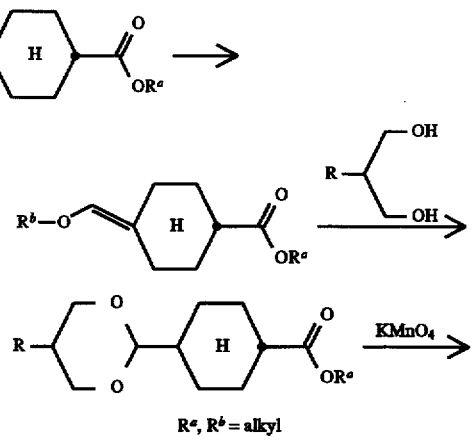

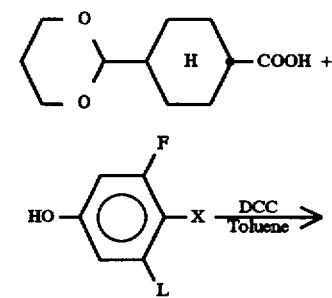

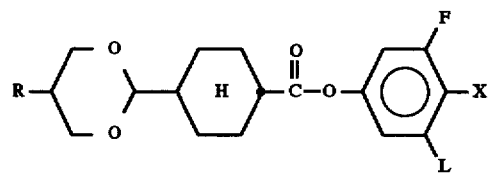

The novel liquid-crystalline media preferably comprise 2 to 40, in particular 4 to 30, components as further constituents besides one or more novel compounds. These media very particularly preferably comprise 7 to 25 components besides one or more novel compounds. These further constituents are preferably selected from nematic or nematogenic (monotropic or isotropic) substances, in particular substances from the classes of the azoxybenzenes, benzylideneanilines, biphenyls, terphenyls, phenyl or cyclohexyl benzoates, phenyl or cyclohexyl-esters of cyclohexanecarboxylic acid, phenyl or cyclohexyl esters of cyclohexylbenzoic acid, phenyl or cyclohexyl esters of cyclohexylcyclohexanecarboxylic acid, cyclohexylphenyl esters of benzoic acid, of cyclohexanecarboxylic acid and of cyclohexylcyclohexanecarboxylic acid, phenylcyclohexanes, cyclohexylbiphenyls, phenylcyclohexylcyclohexanes, cyclohexylcyclohexanes, cyclohexylcyclohexylcyclohexanes, 1,4-bis-cyclohexylbenzenes, 4,4'-biscyclohexylbiphenyls, phenyl- or cyclohexylpyrimidines, phenyl- or cyclohexylpyridines, phenyl- or cyclohexyldioxanes, phenyl- or cyclohexyl-1,3-dithianes, 1,2-diphenylethanes, 1,2-dicyclohexylethanes,1-phenyl-2-cyclohexylethanes, 1-cyclohexyl-2-(4-phenylcyclohexyl)ethanes, 1-cyclohexyl-2-biphenylylethanes, 1-phenyl-2-cyclohexylphenylethanes, optionally halogenated stilbenes, benzyl phenyl ethers, tolans and substituted cinnamic acids. The 1,4-phenylene groups in these compounds may also be fluorinated.

The most important compounds suitable as further constituents of novel media can be characterized by the formulae 1, 2, 3, 4 and 5:

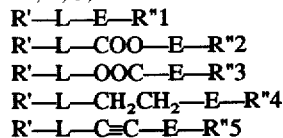

In the formulae 1, 2, 3, 4 and 5, L and E, which may be identical or different, are in each case, independently of one another, a bivalent radical from the group formed by -Phe-, -Cyc-, -Phe-Phe-, -Phe-Cyc-, -Cyc-Cyc-, -Pyr-, -Dio-, -G-Phe- and -G-Cyc-, and their mirror images, where Phe is unsubstituted or fluorine-substituted 1,4-phenylene, Cyc is trans-1,4-cyclohexylene or 1,4-cyclohexylene, Pyr is pyrimidine-2,5-diyl or pyridine-2,5-diyl, Dio is 1,3-dioxane-2,5-diyl and G is 2-(trans-1,4-cyclohexyl)ethyl, pyrimidine-2,5-diyl, pyridine-2,5-diyl or 1,3-dioxane-2,5-diyl.

One of the radicals L and E is preferably Cyc, Phe or Pyr. E is preferably Cyc, Phe or Phe-Cyc. The novel media preferably comprise one or more components selected from the compounds of the formulae 1, 2, 3, 4 and 5 in which L and E are selected from the group consisting of Cyc, Phe and Pyr and simultaneously one or more components selected from the compounds of the formulae 1, 2, 3, 4 and 5 in which one of the radicals L and E is selected from the group consisting of Cyc, Phe and Pyr and the other radical is selected from the group consisting of -Phe-Phe-, -Phe-Cyc-, -Cyc-Cyc-, -G-Phe- and -G-Cyc-, and optionally one or more components selected from the compounds of the formulae 1, 2, 3, 4 and 5 in which the radicals L and E are selected from the group consisting of -Phe-Cyc-, -Cyc-Cyc-, -G-Phe- and -G-Cyc-.

In a smaller sub-group of the compounds of the formulae 1, 2, 3, 4 and 5, R' and R" are in each case, independently of one another, alkyl, alkenyl, alkoxy, alkoxyalkyl, alkenyloxy or alkanoyloxy having up to 8 carbon atoms. This smaller sub-group is called group A below, and the compounds are labelled with the sub-formulae 1a, 2a, 3a, 4a and 5a. In most of these compounds, R' and R" are different from one another, one of these radicals usually being alkyl, alkenyl, alkoxy or alkoxyalkyl.

In another smaller sub-group of the compounds of the formulae 1, 2, 3, 4 and 5 which is known as group B, R" is —F, —Cl, —NCS or —(O)$_i$CH$_{3-(k+1)}$F$_k$Cl$_1$, where i is 0 or 1, and k+1 is 1, 2 or 3; the compounds in which R" has this meaning are labelled with the sub-formulae 1b, 2b, 3b, 4b and 5b. Particular preference is given to those compounds of the sub-formulae 1b, 2b, 3b, 4b and 5b in which R" is —F, —Cl, —NCS, —CF$_3$, —OCHF$_2$ or —OCF$_3$.

In the compounds of the sub-formulae 1b, 2b, 3b, 4b and 5b, R' is as defined for the compounds of the sub-formulae 1a–5a and is preferably alkyl, alkenyl, alkoxy or alkoxyalkyl.

In a further smaller sub-group of the compounds of the formulae 1, 2, 3, 4 and 5, R" is —CN; this sub-group is known as group C below, and the compounds of this sub-group are correspondingly described by sub-formulae 1c, 2c, 3c, 4c and 5c. In the compounds of the sub-formulae 1c, 2c, 3c, 4c and 5c, R' is as defined for the compounds of the sub-formulae 1a–5a and is preferably alkyl, alkoxy or alkenyl.

In addition to the preferred compounds of groups A, B and C, other compounds of the formulae 1, 2, 3, 4 and 5 having other variants of the proposed substituents are also customary. All these substances can be obtained by methods which are known from the literature or analogously thereto.

Besides novel compounds of the formula I, the novel media preferably comprise one or more compounds selected from group A and/or group B and/or group C. The proportions by weight of the compounds from these groups in the novel media are preferably Group A: 0 to 90%, preferably 10 to 90%, in particular 30 to 90%

Group B: 0 to 80%, preferably 10 to 80%, in particular 10 to 65%

Group C: 0 to 80%, preferably 5 to 80%, in particular 5 to 50%, the sum of the proportions by weight of the group A and/or B and/or C compounds present in the particular novel media preferably being 5–90% and in particular 10 to 90%.

The novel media preferably comprise 1 to 40%, particularly preferably 5 to 30%, of novel compounds. Further preferred media are those which comprise more than 40%, in particular 45 to 90%, of novel compounds. The media preferably comprise three, four or five novel compounds.

The novel media are prepared in a manner which is customary per se. In general, the components are dissolved in one another, expediently at elevated temperature. By means of suitable additives, the liquid-crystalline phases can be modified in accordance with the invention in a manner such that they can be used in all types of liquid-crystal display elements which have hitherto been disclosed. Additives of this type are known to those skilled in the art and are described in detail in the literature (H. Kelker/R. Hatz, Handbook of Liquid Crystals, Verlag Chemie, Weinheim, 1980). For example, pleochroic dyes can be added for the preparation of coloured guest-host systems, or substances can be added to modify the dielectric anisotropy, the viscosity and/or the orientation of the nematic phases.

In the present application and in the examples below, the structures of the liquid-crystal compounds are indicated by acronyms, the transformation into chemical formulae taking place as in Tables A and B below. All the radicals C$_n$H$_{2n+1}$ and C$_m$H$_{2m+1}$ are straight-chain alkyl radicals containing n or m carbon atoms respectively. The coding in Table B is self-evident. In Table A, only the acronym for the parent structure is given. In individual cases, the acronym for the parent structure is followed, separated by a hyphen, by a code for the substituents R$^1$, R$^2$, L$^1$ and L$^2$:

| Code for R$^1$, R$^2$, L$^1$, L$^2$ | R$^1$ | R$^2$ | L$^1$ | L$^2$ |
|---|---|---|---|---|
| nm | C$_n$H$_{2n+1}$ | C$_m$H$_{2m+1}$ | H | H |
| nOm | C$_n$H$_{2n+1}$ | OC$_m$H$_{2m+1}$ | H | H |
| nO.m | OC$_n$H$_{2n+1}$ | C$_m$H$_{2m+1}$ | H | H |
| n | C$_n$H$_{2n+1}$ | CN | H | H |
| nN.F | C$_n$H$_{2n+1}$ | CN | H | F |
| nF | C$_n$H$_{2n+1}$ | F | H | H |
| nOF | OC$_n$H$_{2n+1}$ | F | H | H |

-continued

| Code for R¹, R², L¹, L² | R¹ | R² | L¹ | L² |
|---|---|---|---|---|
| nCl | $C_nH_{2n+1}$ | Cl | H | H |
| nF.F | $C_nH_{2n+1}$ | F | H | F |
| nF.F.F | $C_nH_{2n+1}$ | F | F | F |
| nCF₃ | $C_nH_{2n+1}$ | CF₃ | H | H |
| nOCF₃ | $C_nH_{2n+1}$ | OCF₃ | H | H |
| nOCF₂ | $C_nH_{2n+1}$ | OCHF₂ | H | H |
| nS | $C_nH_{2n+1}$ | NCS | H | H |
| rVsN | $C_rH_{2r+1}$—CH=CH—$C_sH_{2s}$— | CN | H | H |
| rEsN | $C_rH_{2r+1}$—O—$C_sH_{2s}$— | CN | H | H |

-continued

| Code for R¹, R², L¹, L² | R¹ | R² | L¹ | L² |
|---|---|---|---|---|
| nAm | $C_nH_{2n+1}$ | $COOC_mH_{2m+1}$ | H | H |

Novel mixtures comprise, in particular, compounds selected from Tables A and B in addition to one or more compounds of the formula I.

TABLE A

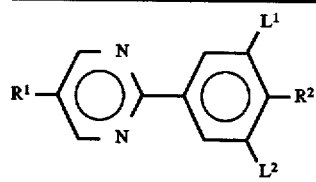

PYP

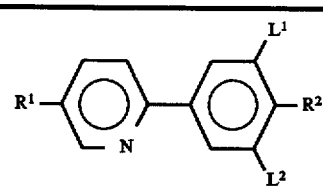

PYRP

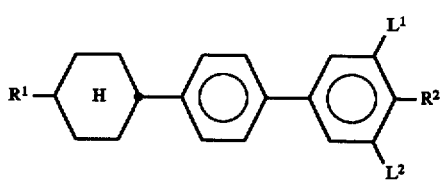

BCH

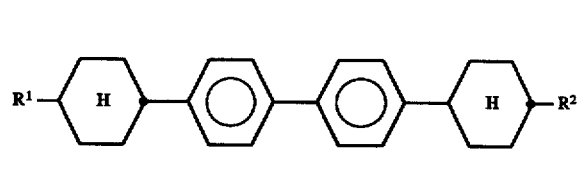

CBC

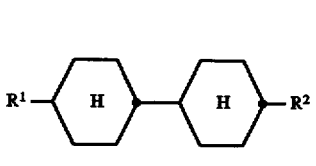

CCH

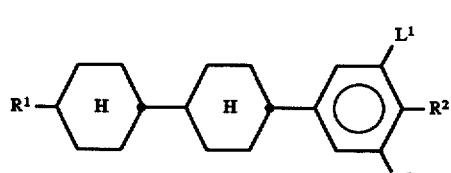

CCP

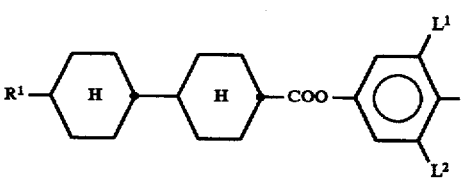

CP

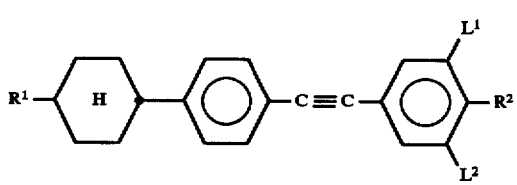

CPTP

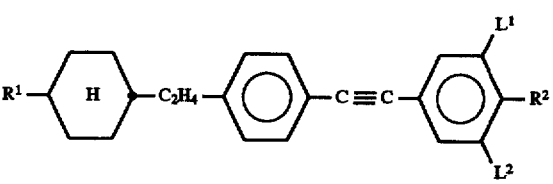

CEPTP

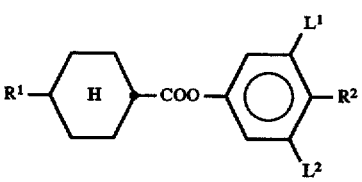

D

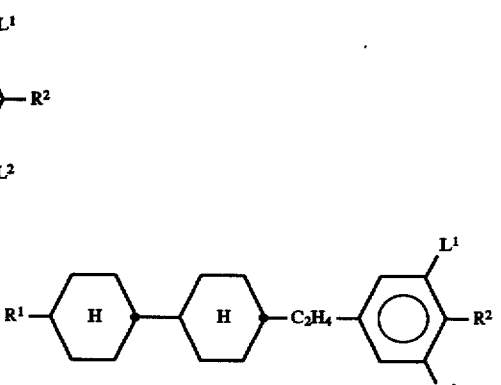

ECCP

TABLE A-continued
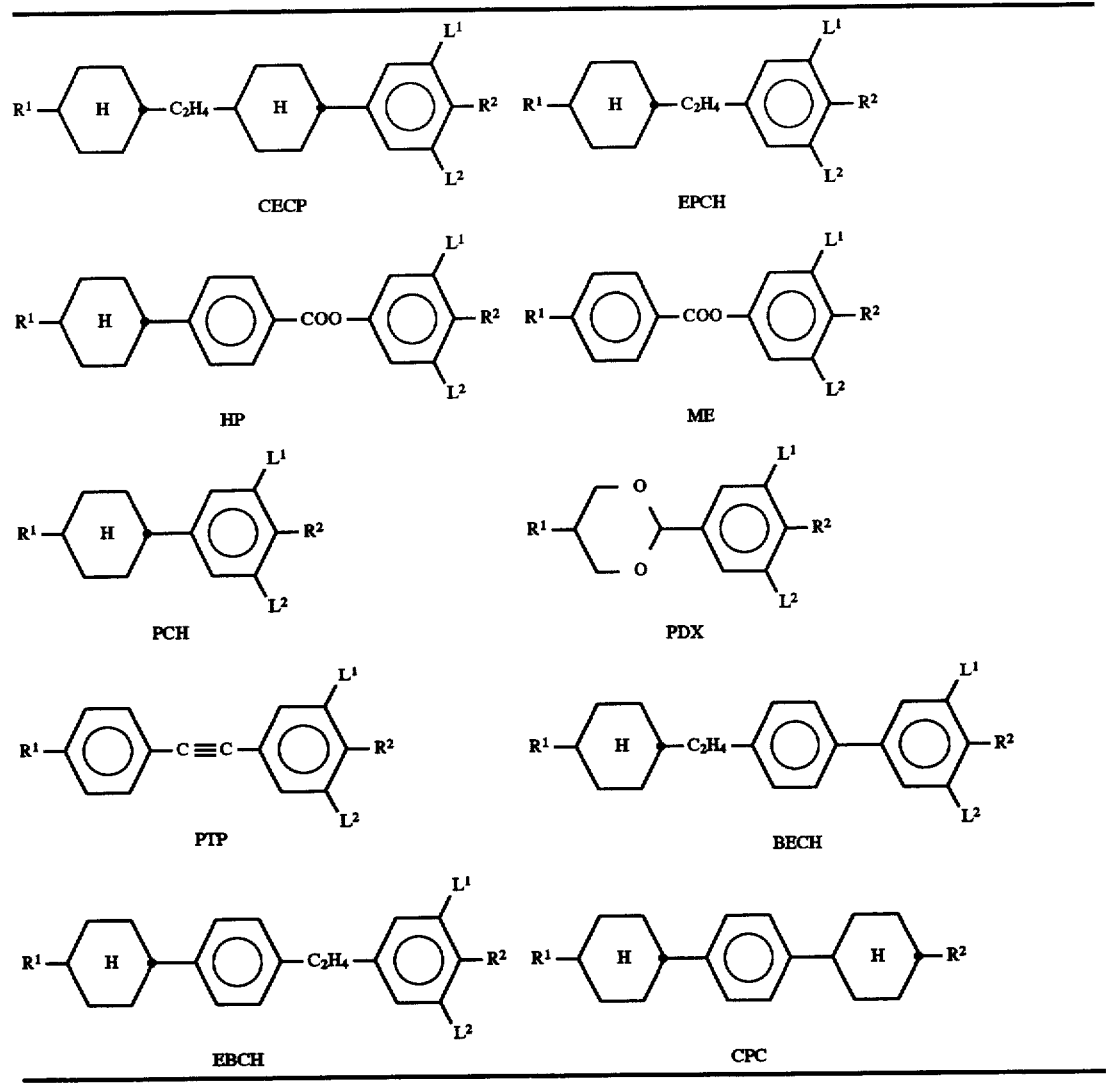
TABLE B
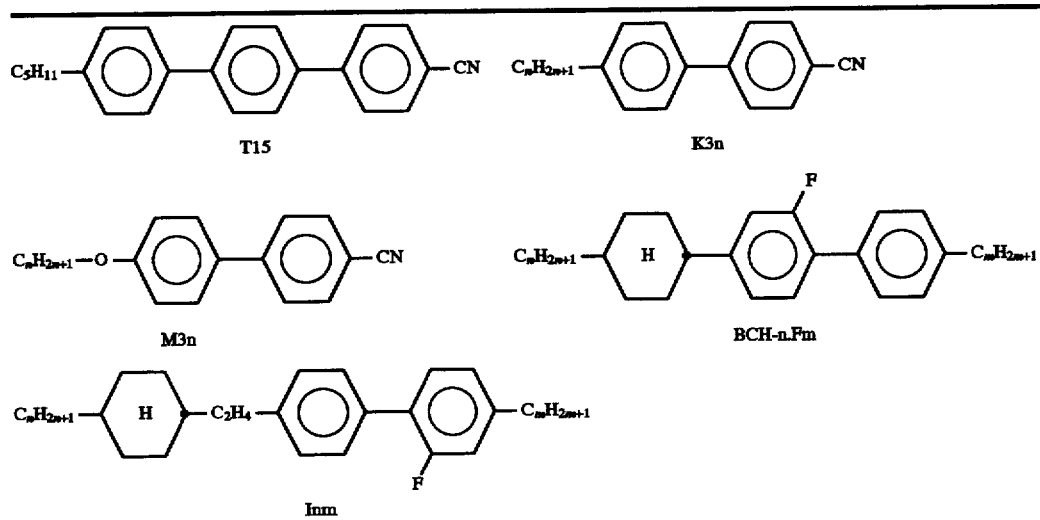

TABLE B-continued
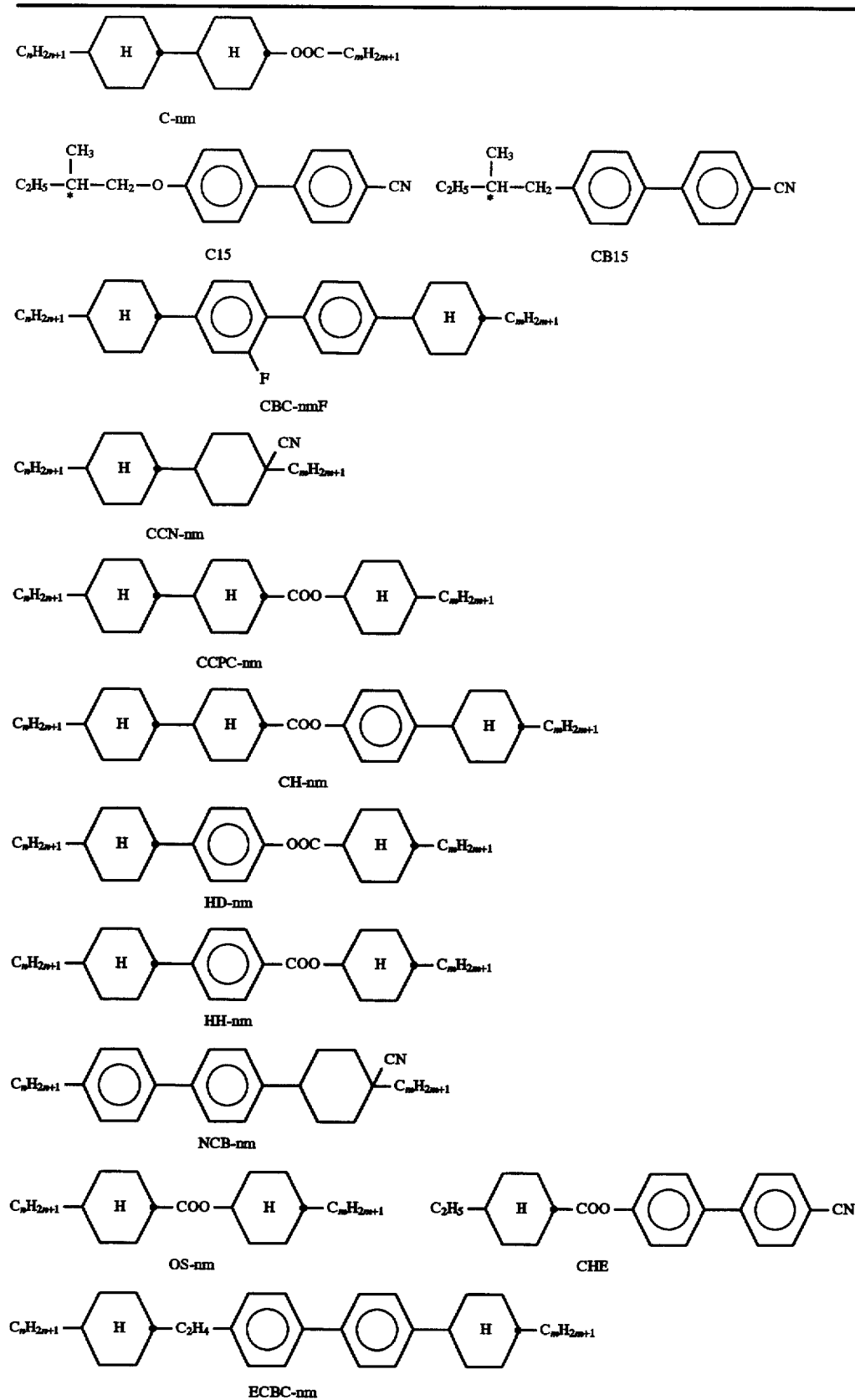

TABLE B-continued

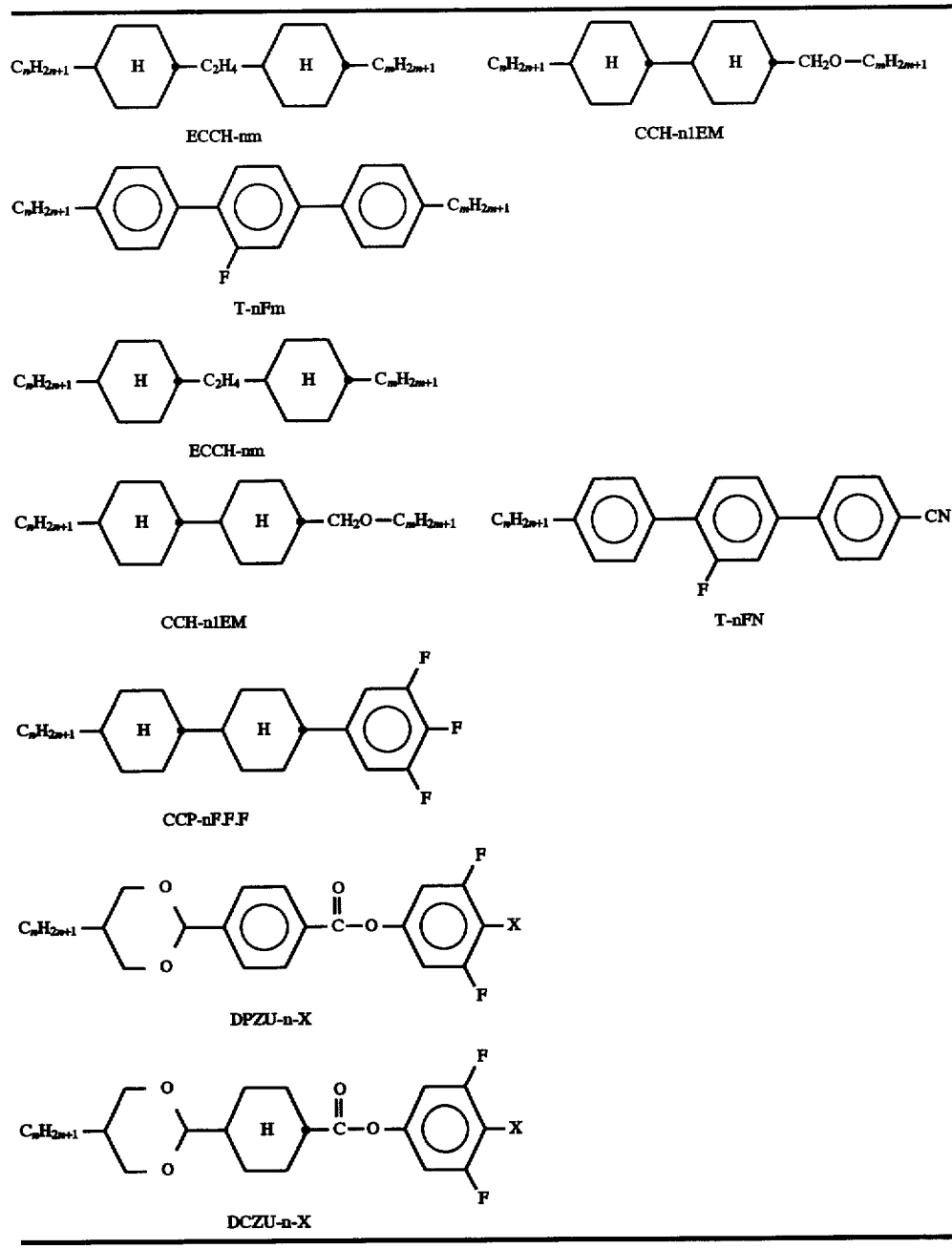

The examples below are intended to illustrate the invention without representing a limitation. Above and below, percentage data are per cent by weight. All temperatures are given in degrees Celsius. mp.=melting point, cp.=clear point. Furthermore, C=crystalline state, N=nematic phase, S=smectic phase and I=isotropic phase. The numbers between these symbols indicate the transition temperatures. An denotes optical anisotropy (589 nm, 20° C.), and the viscosity (mm²/sec) was determined at 20° C.

"Conventional work-up" means that water is added if necessary, the mixture is extracted with dichloromethane, diethyl ether or toluene, the organic phase is separated off, dried and evaporated, and the product is purified by distillation under reduced pressure or crystallization and/or chromatography. The following abbreviations are used:

DCC N,N'-dicyclohexylcarbodiimide
DMAP 4-(dimethylamino)pyridine
POT potassium tertiary-butoxide
THF tetrahydrofuran
pTsOH p-toluenesulfonic acid

EXAMPLE 1

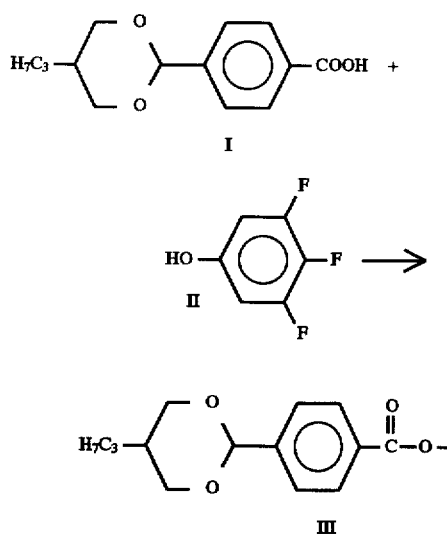

55 mmol of 3,4,5-trifluorophenol in 75 ml of toluene and 55 mmol of DCC are stirred at room temperature for 1 hour. 50 mmol of I are added, and the mixture is stirred overnight at room temperature. 1 g of oxalic acid is then added to the mixture, which is then stirred for a further two hours at room temperature. Finally, the mixture is subjected to conventional work-up. The product is recrystallized from toluene/hexane (1:1). C 111 N (96.7) I.

The following compounds of the formula

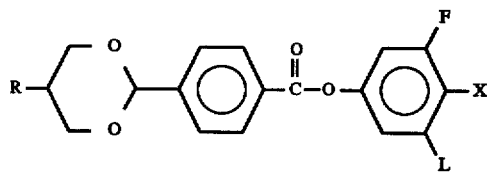

are prepared analogously:

| R | X | L | |
|---|---|---|---|
| CH$_3$ | F | H | |
| CH$_3$ | F | F | |
| C$_2$H$_5$ | F | H | |
| C$_2$H$_5$ | F | F | |
| n-C$_3$H$_7$ | F | H | |
| n-C$_4$H$_9$ | F | H | |
| n-C$_4$H$_9$ | F | F | |
| n-C$_5$H$_{11}$ | F | H | C 94 S$_A$ (92) N 100.2 I; $\Delta n = +0.105$; $\Delta \varepsilon = 30.65$ |
| n-C$_5$H$_{11}$ | F | F | |
| n-C$_6$H$_{13}$ | F | H | |
| n-C$_6$H$_{13}$ | F | F | |
| CH$_3$ | Cl | H | |
| CH$_3$ | Cl | F | |
| C$_2$H$_5$ | Cl | H | |
| C$_2$H$_5$ | Cl | F | |
| n-C$_3$H$_7$ | Cl | H | |
| n-C$_3$H$_7$ | Cl | F | |
| n-C$_4$H$_9$ | Cl | H | |
| n-C$_4$H$_9$ | Cl | F | |
| n-C$_5$H$_{11}$ | Cl | H | |
| n-C$_5$H$_{11}$ | Cl | F | |
| n-C$_6$H$_{13}$ | Cl | H | |
| n-C$_6$H$_{13}$ | Cl | F | |
| CH$_3$ | OCF$_3$ | H | |
| CH$_3$ | OCF$_3$ | F | |
| C$_2$H$_5$ | OCF$_3$ | H | |
| C$_2$H$_5$ | OCF$_3$ | F | |
| n-C$_3$H$_7$ | OCF$_3$ | H | |
| n-C$_3$H$_7$ | OCF$_3$ | F | |
| n-C$_4$H$_9$ | OCF$_3$ | H | |
| n-C$_4$H$_9$ | OCF$_3$ | F | |
| n-C$_5$H$_{11}$ | OCF$_3$ | H | |
| n-C$_5$H$_{11}$ | OCF$_3$ | F | |
| n-C$_6$H$_{13}$ | OCF$_3$ | H | |
| n-C$_6$H$_{13}$ | OCF$_3$ | F | |
| CH$_3$ | CF$_3$ | H | |
| CH$_3$ | CF$_3$ | F | |
| C$_2$H$_5$ | CF$_3$ | H | |
| C$_2$H$_5$ | CF$_3$ | F | |
| n-C$_3$H$_7$ | CF$_3$ | H | |
| n-C$_3$H$_7$ | CF$_3$ | F | |
| n-C$_4$H$_9$ | CF$_3$ | H | |
| n-C$_4$H$_9$ | CF$_3$ | F | |
| n-C$_5$H$_{11}$ | CF$_3$ | H | |
| n-C$_5$H$_{11}$ | CF$_3$ | F | |
| n-C$_6$H$_{13}$ | CF$_3$ | H | |
| n-C$_6$H$_{13}$ | CF$_3$ | F | |
| CH$_3$ | CF$_2$H | H | |
| CH$_3$ | CF$_2$H | F | |
| C$_2$H$_5$ | CF$_2$H | H | |
| C$_2$H$_5$ | CF$_2$H | F | |
| n-C$_3$H$_7$ | CF$_2$H | H | |
| n-C$_3$H$_7$ | CF$_2$H | F | |
| n-C$_4$H$_9$ | CF$_2$H | H | |
| n-C$_4$H$_9$ | CF$_2$H | F | |
| n-C$_5$H$_{11}$ | CF$_2$H | H | |
| n-C$_5$H$_{11}$ | CF$_2$H | F | |
| n-C$_6$H$_{13}$ | CF$_2$H | H | |
| n-C$_6$H$_{13}$ | CF$_2$H | F | |
| CH$_3$ | OCH$_2$CF$_3$ | H | |
| CH$_3$ | OCH$_2$CF$_3$ | F | |
| C$_2$H$_5$ | OCH$_2$CF$_3$ | H | |
| C$_2$H$_5$ | OCH$_2$CF$_3$ | F | |
| n-C$_3$H$_7$ | OCH$_2$CF$_3$ | H | |
| n-C$_3$H$_7$ | OCH$_2$CF$_3$ | F | |
| n-C$_4$H$_9$ | OCH$_2$CF$_3$ | H | |
| n-C$_4$H$_9$ | OCH$_2$CF$_3$ | F | |
| n-C$_5$H$_{11}$ | OCH$_2$CF$_3$ | H | |
| n-C$_5$H$_{11}$ | OCH$_2$CF$_3$ | F | |
| n-C$_6$H$_{13}$ | OCH$_2$CF$_3$ | H | |
| n-C$_6$H$_{13}$ | OCH$_2$CF$_3$ | F | |
| CH$_3$ | OCH=CF$_2$ | H | |
| CH$_3$ | OCH=CF$_2$ | F | |
| C$_2$H$_5$ | OCH=CF$_2$ | H | |
| C$_2$H$_5$ | OCH=CF$_2$ | F | |
| n-C$_3$H$_7$ | OCH=CF$_2$ | H | |
| n-C$_3$H$_7$ | OCH=CF$_2$ | F | |
| n-C$_4$H$_9$ | OCH=CF$_2$ | H | |
| n-C$_4$H$_9$ | OCH=CF$_2$ | F | |
| n-C$_5$H$_{11}$ | OCH=CF$_2$ | H | |
| n-C$_5$H$_{11}$ | OCH=CF$_2$ | F | |
| n-C$_6$H$_{13}$ | OCH=CF$_2$ | H | |
| n-C$_6$H$_{13}$ | OCH=CF$_2$ | F | |
| CH$_3$ | OCHFCF$_3$ | H | |
| CH$_3$ | OCHFCF$_3$ | F | |
| C$_2$H$_5$ | OCHFCF$_3$ | H | |
| C$_2$H$_5$ | OCHFCF$_3$ | F | |
| n-C$_3$H$_7$ | OCHFCF$_3$ | H | |
| n-C$_3$H$_7$ | OCHFCF$_3$ | F | |
| n-C$_4$H$_9$ | OCHFCF$_3$ | H | |
| n-C$_4$H$_9$ | OCHFCF$_3$ | F | |
| n-C$_5$H$_{11}$ | OCHFCF$_3$ | H | |
| n-C$_5$H$_{11}$ | OCHFCF$_3$ | F | |
| n-C$_6$H$_{13}$ | OCHFCF$_3$ | H | |
| n-C$_6$H$_{13}$ | OCHFCF$_3$ | F | |
| CH$_3$ | CF$_3$ | H | |
| CH$_3$ | CF$_3$ | F | |
| C$_2$H$_5$ | CF$_3$ | H | |
| C$_2$H$_5$ | CF$_3$ | F | |
| n-C$_3$H$_7$ | CF$_3$ | H | |
| n-C$_3$H$_7$ | CF$_3$ | F | |
| n-C$_4$H$_9$ | CF$_3$ | H | |
| n-C$_4$H$_9$ | CF$_3$ | F | |

-continued

| | | | |
|---|---|---|---|
| n-C$_5$H$_{11}$ | CF$_3$ | H | |
| n-C$_5$H$_{11}$ | CF$_3$ | F | |
| n-C$_6$H$_{13}$ | CF$_3$ | H | |
| n-C$_6$H$_{13}$ | CF$_3$ | F | |
| CH$_3$ | OCHFCHF$_2$ | H | |
| CH$_3$ | OCHFCHF$_2$ | F | |
| C$_2$H$_5$ | OCHFCHF$_2$ | H | |
| C$_2$H$_5$ | CCHFCHF$_2$ | F | |
| n-C$_3$H$_7$ | OCHFCHF$_2$ | H | |
| n-C$_3$H$_7$ | OCHFCHF$_2$ | F | |
| n-C$_4$H$_9$ | OCHFCHF$_2$ | H | |
| n-C$_4$H$_9$ | OCHFCHF$_2$ | F | |
| n-C$_5$H$_{11}$ | CCHFCHF$_2$ | H | |
| n-C$_5$H$_{11}$ | CCHFCHF$_2$ | F | |
| n-C$_6$H$_{13}$ | OCHFCHF$_2$ | H | |
| n-C$_6$H$_{13}$ | OCHFCHF$_2$ | F | |
| CH$_3$ | OC$_2$F$_5$ | H | |
| CH$_3$ | OC$_2$F$_5$ | F | |
| C$_2$H$_5$ | OC2F$_5$ | H | |
| C$_2$H$_5$ | OC$_2$F$_5$ | F | |
| n-C$_3$H$_7$ | OC$_2$F$_5$ | H | |
| n-C$_3$H$_7$ | CC$_2$F$_5$ | F | |
| n-C$_4$H$_9$ | OC$_2$F$_5$ | H | |
| n-C$_4$H$_9$ | OC$_2$F$_5$ | F | |
| n-C$_5$H$_{11}$ | OC$_2$F$_5$ | H | |
| n-C$_5$H$_{11}$ | OC$_2$F$_5$ | F | |
| n-C$_6$H$_{13}$ | OC$_2$F$_5$ | H | |
| n-C$_6$H$_{13}$ | OC$_2$F$_5$ | F | |
| CH$_3$ | OC$_3$F$_7$ | H | |
| CH$_3$ | OC$_3$F$_7$ | F | |
| C$_2$H$_5$ | OC$_3$F$_7$ | H | |
| C$_2$H$_5$ | OC$_3$F$_7$ | F | |
| n-C$_3$H$_7$ | OC$_3$F$_7$ | H | C65 S$_B$ 157 I; $\Delta n = +0.097$; $\Delta \epsilon = 26$ |
| n-C$_3$H$_7$ | OC$_3$F$_7$ | F | |
| n-C$_4$H$_9$ | OC$_3$F$_7$ | H | |
| n-C$_4$H$_9$ | OC$_3$F$_7$ | F | |
| n-C$_5$H$_{11}$ | OC$_3$F$_7$ | H | |
| n-C$_5$H$_{11}$ | OC$_3$F$_7$ | F | |
| n-C$_6$H$_{13}$ | OC$_3$F$_7$ | H | |
| n-C$_6$H$_{13}$ | OC$_3$F$_7$ | F | |
| CH$_3$ | OCF=CF$_2$ | H | |
| CH$_3$ | OCF=CF$_2$ | F | |
| C$_2$H$_5$ | OCF=CF$_2$ | H | |
| C$_2$H$_5$ | OCF=CF$_2$ | F | |
| n-C$_3$H$_7$ | OCF=CF$_2$ | H | |
| n-C$_3$H$_7$ | OCF=CF$_2$ | F | |
| n-C$_4$H$_9$ | OCF=CF$_2$ | H | |
| n-C$_4$H$_9$ | OCF=CF$_2$ | F | |
| n-C$_5$H$_{11}$ | OCF=CF$_2$ | H | |
| n-C$_5$H$_{11}$ | OCF=CF$_2$ | F | |
| n-C$_6$H$_{13}$ | OCF=CF$_2$ | H | |
| n-C$_6$H$_{13}$ | OCF=CF$_2$ | F | |
| CH$_3$ | OCF$_2$CHFCF$_3$ | H | |
| CH$_3$ | OCF$_2$CHFCF$_3$ | F | |
| C$_2$H$_5$ | OCF$_2$CHFCF$_3$ | H | |
| C$_2$H$_5$ | OCF$_2$CHFCF$_3$ | F | |
| n-C$_3$H$_7$ | OCF$_2$CHFCF$_3$ | H | |
| n-C$_3$H$_7$ | OCF$_2$CHFCF$_3$ | F | |
| n-C$_4$H$_9$ | OCF$_2$CHFCF$_3$ | H | |
| n-C$_4$H$_9$ | OCF$_2$CHFCF$_3$ | F | |
| n-C$_5$H$_{11}$ | OCF$_2$CHFCF$_3$ | H | |
| n-C$_5$H$_{11}$ | OCF$_2$CHFCF$_3$ | F | |
| n-C$_6$H$_{13}$ | OCF$_2$CHFCF$_3$ | H | |
| n-C$_6$H$_{13}$ | OCF$_2$CHFCF$_3$ | F | |

Example 2

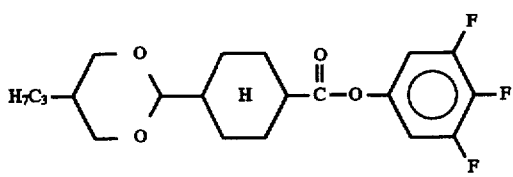

-continued

Step 2.1

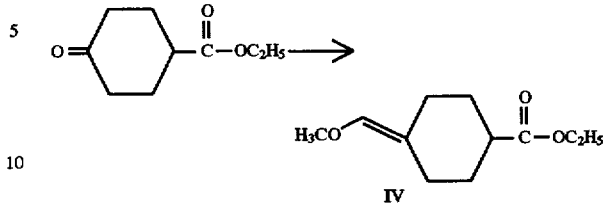

1.5 mol of ethyl cyclohexanonecarboxylate and 1.5 mol of methoxymethyltriphenylphosphonium chloride are suspended in 2 l of methyl tert-butyl ether, and a solution of 1.5 mol of potassium tert-butoxide in 500 ml of THF is added with cooling at $-5°$ C.$\rightarrow +5°$ C. When the addition is complete, the mixture is stirred overnight at room temperature, water and 10 ml of conc. HCl are added, and the mixture is then subjected to conventional work-up.

Step 2.2

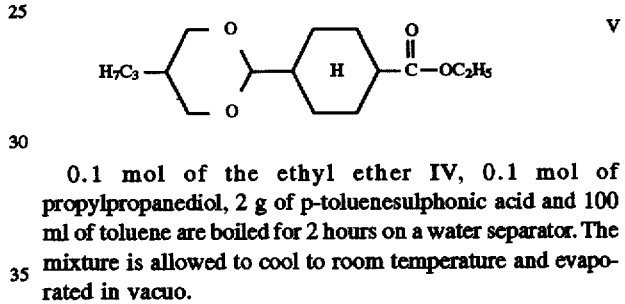

0.1 mol of the ethyl ether IV, 0.1 mol of propylpropanediol, 2 g of p-toluenesulphonic acid and 100 ml of toluene are boiled for 2 hours on a water separator. The mixture is allowed to cool to room temperature and evaporated in vacuo.

Step 2.3

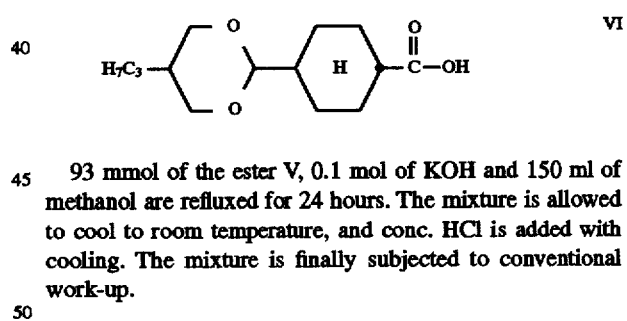

93 mmol of the ester V, 0.1 mol of KOH and 150 ml of methanol are refluxed for 24 hours. The mixture is allowed to cool to room temperature, and conc. HCl is added with cooling. The mixture is finally subjected to conventional work-up.

Step 2.4

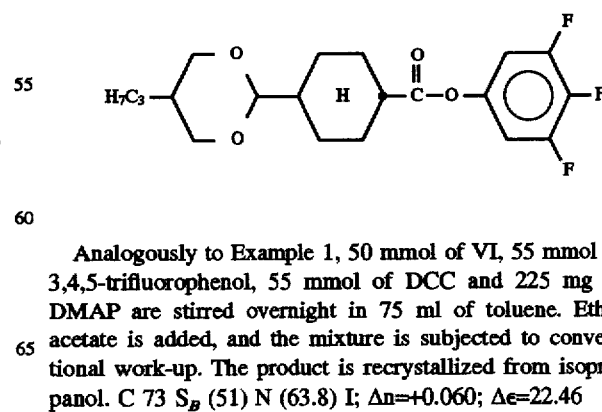

Analogously to Example 1, 50 mmol of VI, 55 mmol of 3,4,5-trifluorophenol, 55 mmol of DCC and 225 mg of DMAP are stirred overnight in 75 ml of toluene. Ethyl acetate is added, and the mixture is subjected to conventional work-up. The product is recrystallized from isopropanol. C 73 S$_B$ (51) N (63.8) I; $\Delta n=+0.060$; $\Delta\epsilon=22.46$ The following compounds of the formula

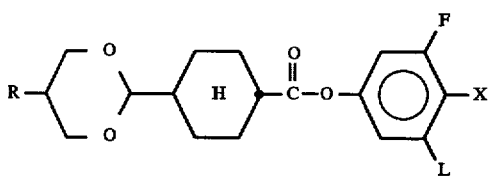

are prepared analogously:

| R | X | L | |
|---|---|---|---|
| CH₃ | F | H | |
| CH₃ | F | F | |
| C₂H₅ | F | H | C 81 S_B (66) N 82.5 I; Δn = +0.062; Δε = 17.7 |
| C₂H₅ | F | F | C 100 I; Δn = +0.044; Δε = 27.4 |
| n-C₃H₇ | F | H | C 82 S_B 92 N 107.7 I; Δn = +0.065; Δε = 17 |
| n-C₄H₉ | F | H | |
| n-C₄H₉ | F | F | |
| n-C₅H₁₁ | F | H | C 69 S_B 90 N 111.5 I; Δn = +0.068; Δε = 15.3 |
| n-C₅H₁₁ | F | F | C 61 S_B (48) N 74.3 I; Δn = +0.061; Δε = 20.0 |
| n-C₆H₁₃ | F | H | |
| n-C₆H₁₃ | F | F | |
| CH₃ | Cl | H | |
| CH₃ | Cl | F | |
| C₂H₅ | Cl | H | |
| C₂H₅ | Cl | F | |
| n-C₃H₇ | Cl | H | |
| n-C₃H₇ | Cl | F | |
| n-C₄H₉ | Cl | H | |
| n-C₄H₉ | Cl | F | |
| n-C₅H₁₁ | Cl | H | |
| n-C₅H₁₁ | Cl | F | |
| n-C₆H₁₃ | Cl | H | |
| n-C₆H₁₃ | Cl | F | |
| CH₃ | OCF₃ | H | |
| CH₃ | OCF₃ | F | |
| C₂H₅ | OCF₃ | H | C 61 S_B 115 I; Δn = +0.065; Δε = 19.7 |
| C₂H₅ | OCF₃ | F | |
| n-C₃H₇ | OCF₃ | H | C 59 S_B 133 I; Δn 32 +0.069; Δε = 19.1 |
| n-C₃H₇ | OCF₃ | F | |
| n-C₄H₉ | OCF₃ | H | |
| n-C₄H₉ | OCF₃ | F | |
| n-C₅H₁₁ | OCF₃ | H | C 45 S_B 136 I; Δn = +0.070; Δε = 17.9 |
| n-C₅H₁₁ | OCF₃ | F | |
| n-C₆H₁₃ | OCF₃ | H | |
| n-C₆H₁₃ | OCF₃ | F | |
| CH₃ | CF₃ | H | |
| CH₃ | CF₃ | F | |
| C₂H₅ | CF₃ | H | |
| C₂H₅ | CF₃ | F | |
| n-C₃H₇ | CF₃ | H | |
| n-C₃H₇ | CF₃ | F | |
| n-C₄H₉ | CF₃ | H | |
| n-C₄H₉ | CF₃ | F | |
| n-C₅H₁₁ | CF₃ | H | |
| n-C₅H₁₁ | CF₃ | F | |
| n-C₆H₁₃ | CF₃ | H | |
| n-C₆H₁₃ | CF₃ | F | |
| CH₃ | CF₂H | H | |
| CH₃ | CF₂H | F | |
| C₂H₅ | CF₂H | H | |
| C₂H₅ | CF₂H | F | |
| n-C₃H₇ | CF₂H | H | |
| n-C₃H₇ | CF₂H | F | |
| n-C₄H₉ | CF₂H | H | |
| n-C₄H₉ | CF₂H | F | |
| n-C₅H₁₁ | CF₂H | H | |
| n-C₅H₁₁ | CF₂H | F | |
| n-C₆H₁₃ | CF₂H | H | |
| n-C₆H₁₃ | CF₂H | F | |
| CH₃ | OCH₂CF₃ | H | |
| CH₃ | OCH₂CF₃ | F | |
| C₂H₅ | OCH₂CF₃ | H | |
| C₂H₅ | OCH₂CF₃ | F | |
| n-C₃H₇ | OCH₂CF₃ | H | |
| n-C₃H₇ | OCH₂CF₃ | F | |
| n-C₄H₉ | OCH₂CF₃ | H | |
| n-C₄H₉ | OCH₂CF₃ | F | |
| n-C₅H₁₁ | OCH₂CF₃ | H | |
| n-C₅H₁₁ | OCH₂CF₃ | F | |
| n-C₆H₁₃ | OCH₂CF₃ | H | |
| n-C₆H₁₃ | OCH₂CF₃ | F | |
| CH₃ | OCH=CF₂ | H | |
| CH₃ | OCH=CF₂ | F | |
| C₂H₅ | OCH=CF₂ | H | |
| C₂H₅ | OCH=CF₂ | F | |
| n-C₃H₇ | OCH=CF₂ | H | |
| n-C₃H₇ | OCH=CF₂ | F | |
| n-C₄H₉ | OCH=CF₂ | H | |
| n-C₄H₉ | OCH=CF₂ | F | |
| n-C₅H₁₁ | OCH=CF₂ | H | |
| n-C₅H₁₁ | OCH=CF₂ | F | |
| n-C₆H₁₃ | OCH=CF₂ | H | |
| n-C₆H₁₃ | OCH=CF₂ | F | |
| CH₃ | OCHFCF₃ | H | |
| CH₃ | OCHFCF₃ | F | |
| C₂H₅ | OCHFCF₃ | H | |
| C₂H₅ | OCHFCF₃ | F | |
| n-C₃H₇ | OCHFCF₃ | H | |
| n-C₃H₇ | OCHFCF₃ | F | |
| n-C₄H₉ | OCHFCF₃ | H | |
| n-C₄H₉ | OCHFCF₃ | F | |
| n-C₅H₁₁ | OCHFCF₃ | H | |
| n-C₅H₁₁ | OCHFCF₃ | F | |
| n-C₆H₁₃ | OCHFCF₃ | H | |
| n-C₆H₁₃ | OCHFCF₃ | F | |
| CH₃ | CF₃ | H | |
| CH₃ | CF₃ | F | |
| C₂H₅ | CF₃ | H | |
| C₂H₅ | CF₃ | F | |
| n-C₃H₇ | CF₃ | H | |
| n-C₃H₇ | CF₃ | F | |
| n-C₄H₉ | CF₃ | H | |
| n-C₄H₉ | CF₃ | F | |
| n-C₅H₁₁ | CF₃ | H | |
| n-C₅H₁₁ | CF₃ | F | |
| n-C₆H₁₃ | CF₃ | H | |
| n-C₆H₁₃ | CF₃ | F | |
| CH₃ | OCHFCHF₂ | H | |
| CH₃ | OCHFCHF₂ | F | |
| C₂H₅ | OCHFCHF₂ | H | |
| C₂H₅ | OCHFCHF₂ | F | |
| n-C₃H₇ | OCHFCHF₂ | H | |
| n-C₃H₇ | OCHFCHF₂ | F | |
| n-C₄H₉ | OCHFCHF₂ | H | |
| n-C₄H₉ | OCHFCHF₂ | F | |
| n-C₅H₁₁ | OCHFCHF₂ | H | |
| n-C₅H₁₁ | OCHFCHF₂ | F | |
| n-C₆H₁₃ | OCHFCHF₂ | H | |
| n-C₆H₁₃ | OCHFCHF₂ | F | |
| CH₃ | OC₂F₅ | H | |
| CH₃ | OC₂F₅ | F | |
| C₂H₅ | OC₂F₅ | H | |
| C₂H₅ | OC₂F₅ | F | |
| n-C₃H₇ | OC₂F₅ | H | |
| n-C₃H₇ | OC₂F₅ | F | |
| n-C₄H₉ | OC₂F₅ | H | |
| n-C₄H₉ | OC₂F₅ | F | |
| n-C₅H₁₁ | OC₂F₅ | H | |
| n-C₅H₁₁ | OC₂F₅ | F | |
| n-C₆H₁₃ | OC₂F₅ | H | |
| n-C₆H₁₃ | OC₂F₅ | F | |
| CH₃ | OC₃F₇ | H | |
| CH₃ | OC₃F₇ | F | |
| C₂H₅ | OC₃F₇ | H | |
| C₂H₅ | OC₃F₇ | F | |
| n-C₃H₇ | OC₃F₇ | H | |

| | | |
|---|---|---|
| n-C₃H₇ | OC₃F₇ | F |
| n-C₄H₉ | OC₃F₇ | H |
| n-C₄H₉ | OC₃F₇ | F |
| n-C₅H₁₁ | OC₃F₇ | H |
| n-C₅H₁₁ | OC₃F₇ | F |
| n-C₆H₁₃ | OC₃F₇ | H |
| n-C₆H₁₃ | OC₃F₇ | F |
| CH₃ | OCF=CF₂ | H |
| CH₃ | OCF=CF₂ | F |
| C₂H₅ | OCF=CF₂ | H |
| C₂H₅ | OCF=CF₂ | F |
| n-C₃H₇ | OCF=CF₂ | H |
| n-C₃H₇ | OCF=CF₂ | F |
| n-C₄H₉ | OCF=CF₂ | H |
| n-C₄H₉ | OCF=CF₂ | F |
| n-C₅H₁₁ | OCF=CF₂ | H |
| n-C₅H₁₁ | OCF=CF₂ | F |
| n-C₆H₁₃ | OCF=CF₂ | H |
| n-C₆H₁₃ | OCF=CF₂ | F |
| CH₃ | OCF₂CHFCF₃ | H |
| CH₃ | OCF₂CHFCF₃ | F |
| C₂H₅ | OCF₂CHFCF₃ | H |
| C₂H₅ | OCF₂CHFCF₃ | F |
| n-C₃H₇ | OCF₂CHFCF₃ | H |
| n-C₃H₇ | OCF₂CHFCF₃ | F |
| n-C₄H₉ | OCF₂CHFCF₃ | H |
| n-C₄H₉ | OCF₂CHFCF₃ | F |
| n-C₅H₁₁ | OCF₂CHFCF₃ | H |
| n-C₅H₁₁ | OCF₂CHFCF₃ | F |
| n-C₆H₁₃ | OCF₂CHFCF₃ | H |
| n-C₆H₁₃ | OCF₂CHFCF₃ | F |
| n-C₃H₇ | OCHFCHF₂ | H |
| n-C₃H₇ | OCHFCHF₂ | F |
| n-C₅H₁₁ | OCHFCHF₂ | H |
| n-C₅H₁₁ | OCHFCHF₂ | F |
| CH₂=CH | F | H |
| CH₂=CH | F | F |
| CH₃—CH=CH | F | H |
| CH₃—CH=CH | F | F |
| CH₂=CH—C₂H₄— | F | H |
| CH₂=CH—C₂H₄— | F | F |
| CH₃CH=CH—C₂H₄ | F | H |
| CH₃CH=CH—C₂H₄ | F | F |

Mixture examples

Example A

| | | |
|---|---|---|
| PCH-5F | 9.50% | Clearing point [°C.]: 92.5 |
| PCH-6F | 7.60% | Δn [589 nm, 20° C.]: 0.0977 |
| PCH-7F | 5.70% | Δε [1 kHz, 20° C.]: 7.34 |
| CCP-2OCF₃ | 7.60% | |
| CCP-3OCF₃ | 11.40% | |
| CCP-4OCF₃ | 8.55% | |
| CCP-5OCF₃ | 8.55% | |
| BCH-3F.F | 11.40% | |
| BCH-5F.F | 9.50% | |
| ECCP-3OCF₃ | 4.75% | |
| ECCP-5OCF₃ | 4.75% | |
| CBC-33F | 1.90% | |
| CBC-53F | 1.90% | |
| CBC-55F | 1.90% | |
| DBZU-3F | 5.00% | |

Example B

| | |
|---|---|
| PCH-5F | 9.50% |
| PCH-6F | 7.60% |
| PCH-7F | 5.70% |
| CCP-2OCF₃ | 7.60% |
| CCP-3OCF₃ | 11.40% |
| CCP-4OCF₃ | 8.55% |
| CCP-5OCF₃ | 8.55% |
| BCH-3F.F | 11.40% |
| BCH-5F.F | 9.50% |
| ECCP-3OCF₃ | 4.75% |
| ECCP-5OCF₃ | 4.75% |
| CBC-33F | 1.90% |
| CBC-53F | 1.90% |

| | |
|---|---|
| CBC-55F | 1.90% |
| DBZU-3-F | 5.00% |

The preceding examples can be repeated with similar success by substituting the generically or specifically described reactants and/or operating conditions of this invention for those used in the preceding examples.

The entire disclosures of all applications, patents and publications cited above, and of corresponding application German P 195 49 123.8, filed Dec. 29, 1995, are hereby incorporated by reference.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A 1,3-dioxane of the formula I

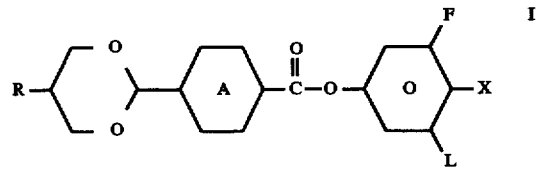

in which

R is H, an alkyl or alkenyl radical having 1 to 15 carbon atoms which is unsubstituted, monosubstituted by CN or CF₃ or at least monosubstituted by halogen, where, in addition, one or more CH₂ groups in these radicals can be replaced, in each case independently of one another, by —O—, —S—,

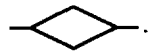

—CO—, —CO—O—, —O—CO— or —O—CO—O— in such a way that O atoms are linked directly to one another,

is (a) trans-1,4-cyclohexylene,
(b) 1,4-phenylene, in which one or two CH groups can also be replaced by N,
(c) 1,4-cyclohexenylene, where the radicals (b) and (c) can be monosubstituted or polysubstituted by fluorine, X is F, Cl, halogenated alkyl, alkoxy or alkenyl having 1–5 carbon atoms, and L is H or F;

provided that, when X is F or Cl, L is F.

2. A 1,3-dioxane of claim 1, which is of the formula I1

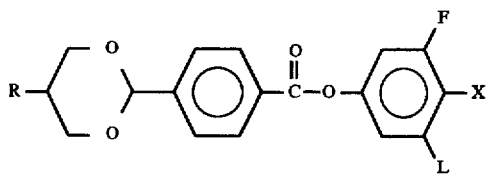

in which R, X and L are as defined.

3. A 1,3-dioxane of claim 1, which is of the formula I2

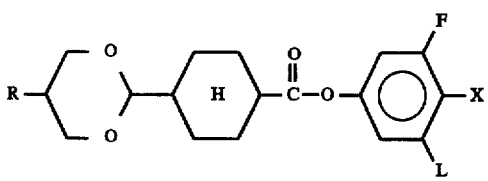

in which R, X and L are as defined.

4. A 1,3-dioxane according to claim 1, wherein X is F, Cl, $OCF_3$, $OCHF_2$, $OCH_2CF_3$, $OCHFCF_3$, $OCH=CF_2$, $OCF=CF_2$ or $OC_2F_5$.

5. A 1,3-dioxane according to claim 1, wherein R is a straight-chain alkyl or alkenyl radical having 1 to 5 carbon atoms.

6. A 1,3-dioxane according to claim 1, wherein X=L=F.

7. A liquid-crystalline medium comprising at least two liquid-crystalline components, wherein at least one liquid-crystalline component is a 1,3-dioxane of the formula of claim 1.

8. A liquid-crystal display element, which that it comprises a liquid-crystalline medium according to claim 7.

9. An electro-optical display element, which contains, as dielectric, a liquid-crystalline medium according to claim 7.

10. A 1,3-dioxane according to claim 1, wherein L is F.

11. A 1,3-dioxane according to claim 1, having a dielectric anisotropy, $\Delta\epsilon$, of from 15.3 to 30.65.

* * * * *